United States Patent
Cao et al.

(10) Patent No.: US 9,902,684 B2
(45) Date of Patent: Feb. 27, 2018

(54) **COMPOUND ISOLATED FROM *ISODON FORRESTII* VAR. *FORRESTII* AND PREPARATION METHOD AND APPLICATIONS THEREOF**

(71) Applicant: JIANGSU PROVINCE INSTITUTE OF TRADITIONAL CHINESE MEDICINE, Nanjing (CN)

(72) Inventors: Peng Cao, Nanjing (CN); Jianxin Pu, Nanjing (CN); Xiaoyan Sun, Nanjing (CN); Handong Sun, Nanjing (CN); Weiguang Wang, Nanjing (CN); Jiao Chen, Nanjing (CN); Xueting Cai, Nanjing (CN); Xue Du, Nanjing (CN)

(73) Assignee: JIANGSU PROVINCE INSTITUTE OF TRADITIONAL CHINESE MEDICINE, Nanjing (CN)

( * ) Notice: Subject to any disclaimer, the term of this patent is extended or adjusted under 35 U.S.C. 154(b) by 10 days.

(21) Appl. No.: 15/432,593

(22) Filed: Feb. 14, 2017

(65) Prior Publication Data
US 2017/0174611 A1   Jun. 22, 2017

(30) Foreign Application Priority Data
Dec. 21, 2016  (CN) .......................... 2016 1 1186134

(51) Int. Cl.
| | |
|---|---|
| A61K 31/222 | (2006.01) |
| C07C 69/12 | (2006.01) |
| C07C 69/21 | (2006.01) |
| A61K 36/00 | (2006.01) |

(52) U.S. Cl.
CPC .............. *C07C 69/21* (2013.01); *A61K 36/00* (2013.01); *C07C 69/12* (2013.01); *C07C 2103/86* (2013.01); *C07C 2603/86* (2017.05)

(58) Field of Classification Search
CPC ............................. A61K 31/222; C07C 69/12
USPC ......................................................... 514/511
See application file for complete search history.

(56) References Cited

PUBLICATIONS

Baker et al, J. Lab. Clin. Med (2006), pp. 83-90.*
Welsh et al, Cancer Research (2002), pp. 5089-5095.*
Karlenius and Tonissen, "Thioredoxin and Cancer: A role for Thioredoxin in all states of tumor oxygenation," Cancers (2010, vol. 2, pp. 209-232.*
Yang et al, "Chemical constituents of Abies delavayi," Phytochemistry (2014), vol. 105, pp. 164-170.*

* cited by examiner

*Primary Examiner* — Craig D Ricci
*Assistant Examiner* — Janet L. Coppins
(74) *Attorney, Agent, or Firm* — CBM Patent Consulting, LLC (57) ABSTRACT

A compound of Formula I or pharmaceutically acceptable salt thereof and its preparation method and applications, the new structure of the compound of formula I has not been reported in literature. It is isolated from *Isodon forrestii* var. *forrestii* and can be a compound served as Trx1 selective inhibitor. The present invention further discloses a pharmaceutical composition, preparation of the compound of Formula I and its applications in preparing medicines for preventing or treating cancer. Iso A of the present invention has the advantages of low toxicity, high safety and strong pharmacological effect, which suggests a potential prospect in pharmaceutical applications.

7 Claims, 8 Drawing Sheets

COMPOUND ISOLATED FROM *ISODON FORRESTII* VAR. *FORRESTII* AND PREPARATION METHOD AND APPLICATIONS THEREOF

This application claims priority to Chinese Patent Application Ser. No. CN2016111861342 filed on 21 Dec. 2016.

TECHNICAL FIELD

The present invention belongs to the pharmaceutical industry, in particular, relates to a compound isolated from *Isodon forrestii* var. *forrestii* and preparation method and application thereof.

BACKGROUND

The thioredoxin (Trx) system, comprising Trx, thioredoxin reductase (TrxR) and nitotinamide adeninedinucleotide phosphate (NADPH), is a widespread NADPH dependent disulfide reductase system. There are two distinct isoforms of human thioredoxin, Trx1 and Trx2, which have similar functions. Trx1 and Trx2 localized in different organelles: Trx1 predominantly in cytosol, nucleus and extracellular matrix, and Trx2 in mitochondria. Trx1, a protein with 105 amino acids, possesses the highly conserved cysteine-glycine-proline-cysteine (-Cys-Gly-Pro-Cys-) active site motif. Initially, Trxs bind noncovalently to a target protein disulfide (X-S2) through a hydrophobic surface area surrounding the active site. Next, the sulfhydryl groups of Cys32 act as a nucleophile and attack the target disulfide to form a covalent mixed disulfide intermediate, followed by a nucleophilic attack of the deprotonation of Cys35 on the intermediate intermolecular disulfide bond. This results in the release of reduced substrate protein.

Therefore, Trxs play a vital role in regulating cellular growth and modulating programmed cell apoptosis.by maintaining cellular redox balance.

Accumulating evidence showed that the thioredoxin system is extensively involved in tumor initiation and progresson. Trx1 is overexpressed in many malignant cells and tumor tissues (Anticancer Res 2003; 23:2425-33). overexpression of Trx1 can promote tumor cell proliferation and help the tumor cells evade apoptosis through binding to apoptosis signal regulating kinase-1 (ASK1) and the tumor suppressor phosphatase and tensin homolog (EMBO J 1998; 17: 2596-606, Arch Biochem Biophys 2004; 429: 123-33). Trx1 stimulates sustained angiogenesis in tumors through increasing hypoxia-inducible factor 1α (HIFα) level and enhancing vascular endothelial growth factor (VEGF) function (Cancer Res 2002; 62: 5089-95). Moreover, overexpression of Trx1 expression is clinically correlated to poor prognosis of tumor patients (Cancer Res 2000; 60: 2281-9). In addition to tumor, many other diseases are related to the abnormal cellular response resulted from events mediated by above thioredoxin system. These diseases include, but not limited to, acute and chronic inflammatory diseases, autoimmune diseases, allergic diseases, diseases related to oxidative stress, cancer and diseases characterized by excessive cellular proliferation.

The development of selective Trx1 inhibitors is of great significance in the therapy of Trx1-mediated diseases. An effective inhibitor of Trx1, methylpropyl-2-imidazole disulfide PX-12, has been identified via great efforts in pharmaceutical chemistry Trx1 effectively—(Biochem. Pharmacol 1998; 55: 987-994). PX-12 reversibly formed a disulfide on the active sites of Trx1 and induced the oxidation of Trx1, which disrupts the dimerization of Trx1 and inhibits Trx-TrxR signaling pathway. Pitifully, the clinical trial of PX-12 is unfavorable (Cancer Chemother Pharmacol. 2011; 67: 503-09, Invest New Drugs.2013; 31: 631-41). Therefore, it is of great need to explore novel Trx1 specific inhibitors for pharmaceutical research. These new-developed Trx1 inhibitors may be extreme effective medicines in treating tumors and other Trx1-mediated diseases.

Our country has abundant resources of traditional Chinese medicine. Large amounts of lead compounds are provided by this treasuries house for selecting medicines for treating diseases. Some plants in *Isodon* genus are a folk traditional Chinese herbals and were widely used in our country. Plants in *Isodon* genus are spicy, bitter and cool. Some whole plants and roots were used as medicine having such effects as clearing heat and promoting diuresis, promoting blood circulation to remove blood stasis, removing toxicity for detumescence etc. Plants of this genus enriches with bioactive diterpenoids with various structure, in particular, with ent-kauranoid. Part of diterpenoids have such activities as tumor resistance, immunosuppression, and the effective ingredients of some *Isodon* genus have been applied for clinical use. *Isodon forrestii* var. *forrestii*, which is originated in Northwestern Yunnan and Southwestern Sichuan, is a perennial herb with a wood, rough, pimple-like root. In our country folk, it is used to treat diseases as hot and humid jaundice, stranguria, edema, sore throat, arthragia, amenorrhea, mastitis, hemorrhoids, carbuncle of the back, bruises, venomous snake bites etc. However, Iso A, the diterpenoid obtained form *I. forrestii* var. *forrestii*, has not been reported in literature, and it is still unclear for the application of this effective compound in this plant in preparing antitumor drugs, especially for the relation with thioredoxin signal path.

SUMMARY

The technical problem to be solved by the present invention is to provide a new compound that has not been reported in literature and is served as Trx selective inhibitor, or its pharmaceutically acceptable salt, a pharmaceutical composition consisting of it that serves as effective ingredient and as at least one pharmaceutically acceptable carrier and its preparation method and applications.

In order to solve the above technical problem, the present invention employs the following technical solutions:

A compound of Formula I or pharmaceutically acceptable salt thereof:

I

A preparation method for the compound of Formula I or pharmaceutically acceptable salt thereof comprises steps as follows:

(1) Grinding the aerial parts of *Isodon forrestii* var. *forrestii* into powder;

(2) Soaking the plant powder acquired in step (1) in a mixture of a first organic solvent and water, and a leach solution is obtained by isolating the solid parts;
(3) After the leach solution acquired in step (2) is distilled to remove the first organic solvent, a second organic solvent is added for extraction, and an extract is obtained after the organic phase is concentrated;
(4) Obtaining the compound I according to claim 1 by chromatography and reverse phase silica gel column chromatography on the extract acquired from step (3).

In step (1), the aerial parts of plant is *Isodon forrestii* var. *forrestii*.

In step (2), the mass percentage of the first organic solvent and water in the mixture is 10-100%, the first organic solvent is selected from one or more of methanol, ethanol, chloroform, dichloromethane, petroleum ether or acetone; the soaking method is to soak for 1-3 times, preferably 3 times, in room temperature, the total mass percentage of the plant powder and that soaked in the mixture is 1:1-1:5 kg/L, preferably is 1:1.2-1:2 kg/L.

In step (3), the second organic solvent is one or more of ethyl acetate, chloroform, ether, petroleum ether, preferably is ethyl acetate, the volume ratio of the second organic solvent and the mixture in step (2) is 1:1-1:5.

In step (4), the experimental conditions of the silica gel column chromatography are: the pore diameter of filler silica gel is 100-300 mesh, preferably is 200~300 mesh, the eluent is a mixture of chloroform and acetone with volume ratio of 1:0-1, preferably of 1:0.11~1:0.5; the amounts of the eluent is 3-6 times the total amounts of all specimen plus silica gel; the experimental conditions of the reverse phase silica gel column chromatography are: the type of the reverse phase silica gel is RP-18, the eluent is a mixture of methanol and water or acetonitrile and water with volume ratio of 1:0-1, preferably 73%-85% mixture of methanol and water or acetonitrile and water, the amounts of the eluent is 3-6 times the amounts of used filler RP-18.

The preparation method further includes steps of forming salt with acid, the acids are selected from a group of hydrochloric acid, hydrobromic acid, nitric acid, sulfuric acid, phosphoric acid, tartaric acid, citric acid, formic acid, acetic acid, oxalic acid or other suitable organic acids or inorganic acids.

A pharmaceutical composition comprises the compound or pharmaceutically acceptable salt thereof according to Formula 1.

A pharmaceutical preparation comprises a therapeutically effective amount of pharmaceutically acceptable excipients of the compound or pharmaceutically acceptable salt thereof according to Formula 1. The excipients may be any additives or accessories allowed to be added into the pharmaceutical preparation in addition to active ingredients.

The preparation may be formed as a preparation suited for oral absorption or injection delivery; wherein, the forms of the oral absorption are tablets, sustained-release tablets, controlled release tablets, lozenge, hard or soft capsules, dropping pills, pellets, water suspension concentrate or oil flowable concentrate, emulsions, dispersible powders or granules, oral solution or elixirs, the forms of the injection delivery are sterile water or oil solutions, sterile powders, lipids, emulsions, microemulsions, nanoemulsions or microcapsule.

Applications of the compound of formula I or pharmaceutically acceptable salt thereof or its pharmaceutical composition in preparing medicines are used for preventing and treating a tumor, the tumor is Trx1-mediated tumor.

The compound in the structure of Formula I, called as Isoforresin A, abbreviated as Iso A, is an ent-kaurane diterpene. Through a series of model experiments, it is testified that Iso A can selectively inhibit human tumor cell from growing and induce apoptosis.

Beneficial effect: Iso A in the present invention has a strong pharmacological effect with safety, low toxicity predicts a better prospect in pharmaceutical application.

DETAILED DESCRIPTION

The present invention will be better understood from the following examples. However, it will be readily understood by those skilled in the art that the description of the embodiments is for the purpose of illustrating the invention and should not limit the invention as detailed in the claims.

Embodiment 1 Method for preparing compound Iso A

Grinding the aerial parts of *Isodon forrestii* var. *forrestii* to 10 Kg powder, soaking this powder with total 12 liters of 70% (acetone:water) acetone water in room temperature for three times, after evaporating the acetone by vacuum distillation, the remainder is extracted by ethyl acetate to get ethyl acetate extract. After washing by silica gel column chromatography with silica gel of 200 mesh pore diameter and chloroform:acetone (1:0.11 volume ratio) solvent, 500 mg Iso A can be finally obtained through repeated treatment by RP-18 mixture of etho-methanol and water with 85% volume ratio, and the yield is 0.005%.

The physical and chemical data for X ray single crystal and ultraviolet, optical rotation, infrared, nuclear magnetic resonance etc. of compound Iso A are:

Crystal data for Sze1:$C_{28}H_{38}O_{10}$, M=534.58, orthorhombic, $\alpha$=7.8960(2) Å, b=11.7330(3) Å, c=30.2738(9) Å, $\alpha$=90.00°, $\gamma$=90.00°, $\gamma$=90.00°, V=2804.68(13) Å$^3$, T=100 (2) K, space group P212121, Z=4, $\mu(CuK\alpha)$=0.796 mm$^{-1}$, 12890 reflections measured, 4629 independent reflections ($R_{int}$=0.0457). The final $R_1$ values were 0.0721 (I>2σ(I)). The final wR(F$^2$) values were 0.2147 (I>2σ(I)). The final $R_1$ values were 0.0731 (all data). The final wR(F$^2$) values were 0.2158 (all data). The goodness of fit on F$^2$ was 1.136. Flack parameter=−0.1(3). The Hooft parameter is 0.01(8) for 1779 Bijvoet pairs.

Isoforretin A: Colorless needle crystals. $[\alpha]_D^{25}$=−45.3 (c 0.08, MeOH). UV (MeOH) $\lambda_{max}$ (log ε): 232 (3.9) nm; IR (KBr) V$_{max}$ 3442, 2962, 2934, 2881, 1732, 1644, 1428, 1370, 1251, 1231, 1176, 1034, 995, 603; Positive ESIMS: m/z 557 [M+Na]$^+$; positive HRESIMS [M+Na]$^+$ m/z 557.2365 (calcd for $C_{28}H_{38}O_{10}Na$, 557.2357); $^1$H NMR (600 MHz, $C_5D_5N$) $\delta_H$ 6.17 (1H, s, H-17a), 5.66 (1H, dd, 11.8, 5.5, H-2α), 5.47 (1H, br d, 4.7, H-11α), 5.41 (1H, s, H-17b), 5.37 (1H, br s, H-3α), 5.15 (1H, br s, H-12β), 4.67 (1H, br s, H-6β), 3.34 (1H, br d, 14.5, H-14a), 3.28 (1H, br s, H-13α), 2.58 (1H, br d, 14.2, H-7a), 2.18 (1H, overlap, H-1a), 2.14 (3H, s, Me-20), 2.01 (3H, s, AcO-3), 1.98 (1H, overlap, H-9β), 1.93 (3H, s, AcO-2), 1.87 (1H, overlap, H-1b), 1.83 (1H, overlap, H-7b), 1.74 (3H, s, AcO-11), 1.67 (1H, br d, 14.5, H-14b), 1.61 (3H, s, Me-19), 1.06 (3H, s, Me-18); $^{13}$C NMR (150 MHz, $C_5D_5N$) $\delta_C$ 208.3 (s, C-15), 170.8 (s, AcO-3), 170.4 (s, AcO-2), 169.4 (s, AcO-12), 168.7 (s, AcO-11), 145.4 (s, C-16), 117.1 (t, C-17), 77.9 (d, C-3), 75.4 (d, C-12), 70.1 (d, C-11), 67.9 (d, C-2), 64.9 (d, C-6), 60.2 (d, C-9), 49.8 (d, C-5), 48.8 (s, C-8), 42.7 (t, C-7), 41.8 (d, C-13), 40.8 (t, C-1), 40.3 (s, C-10), 39.0 (s, C-4), 32.2 (t, C-14), 28.7 (q, C-18), 23.4 (q, C-19), 21.1 (q, C-20), 21.1 (q, AcO-2), 21.1 (q, AcO- 11), 20.7 (q, AcO-12), 19.3 (q, AcO-3).

Embodiment 2 Method for preparing compound Iso A

Grinding the aerial parts of *Isodon forrestii* var. *forrestii* to 10 Kg powder of, soaking this powder with total 20 liters of 80% (acetone:water) acetone water in room temperature for three times, after evaporating the acetone by vacuum distillation, the remainder is extracted by ethyl acetate to get ethyl acetate extract. After washing by silica gel column chromatography with silica gel of 300 mesh pore diameter and chloroform:acetone (1:0.5 volume ratio) solvent, 400 mg Iso A can be finally obtained through repeated treatment by RP-18 mixture of acetonitrile and water with 85% volume ratio, and the yield is 0.004%.

Figure 1:
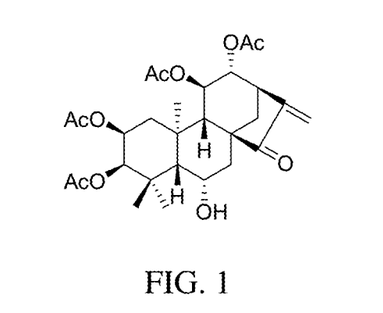
FIG. 1 is a structure view of Iso A.
Figure 2:
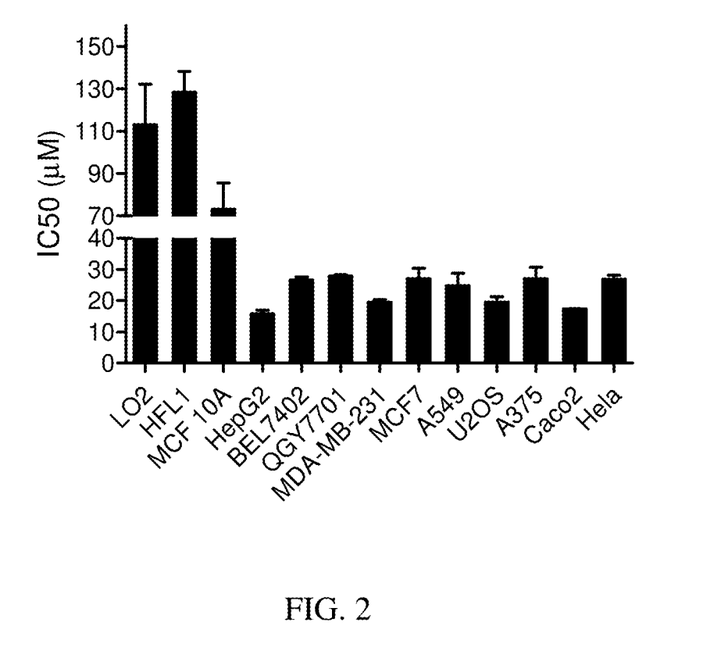
FIG. 2 illustrates $IC_{50}$ values of Iso A for various normal cells and tumor cells in MTT experiment.
Figure 3:
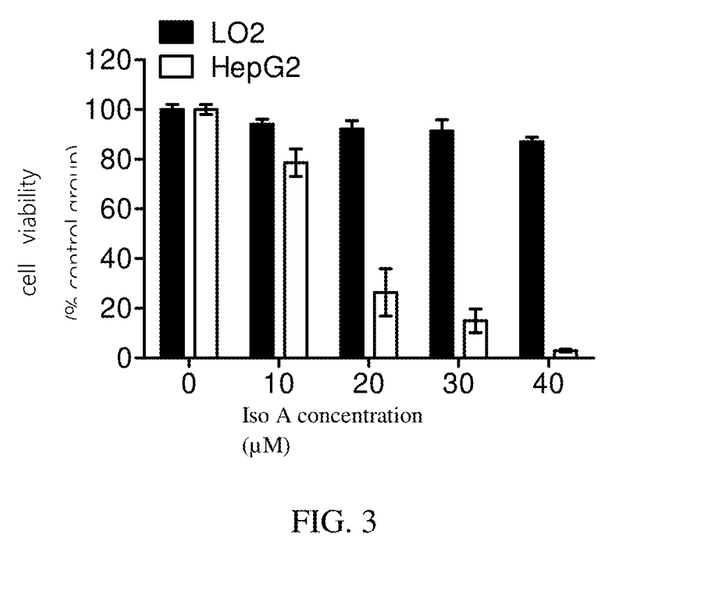
FIG. 3 illustrates the inhibition of cellular growth on human normal hepatic cell line L02 and hepatocellular carcinoma cell line HepG2 after treated by various concentrations of Iso A treated for 24 hours through MTT assay.
Figure 4:
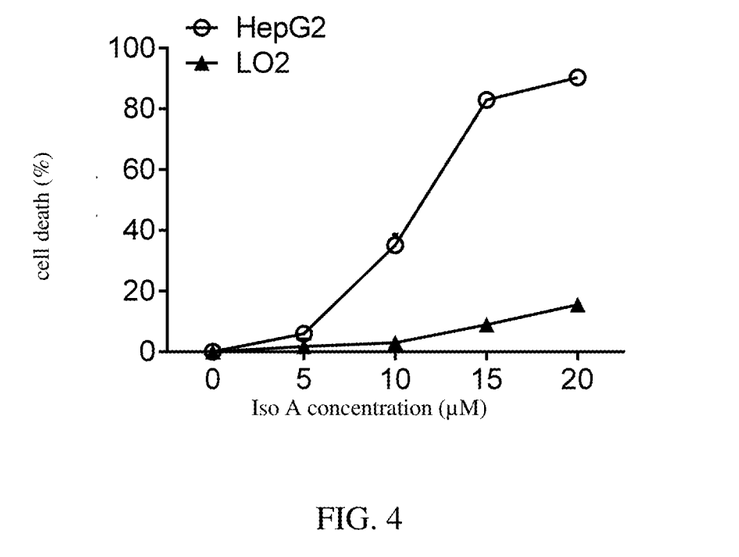
FIG. 4 illustrates the survival results of human normal hepatic cell L02 and hepatocellular carcinoma cell HepG2 after treated by various concentrations of Iso A for 24 hours by Trypan Blue exclusion assay.
Figure 5:
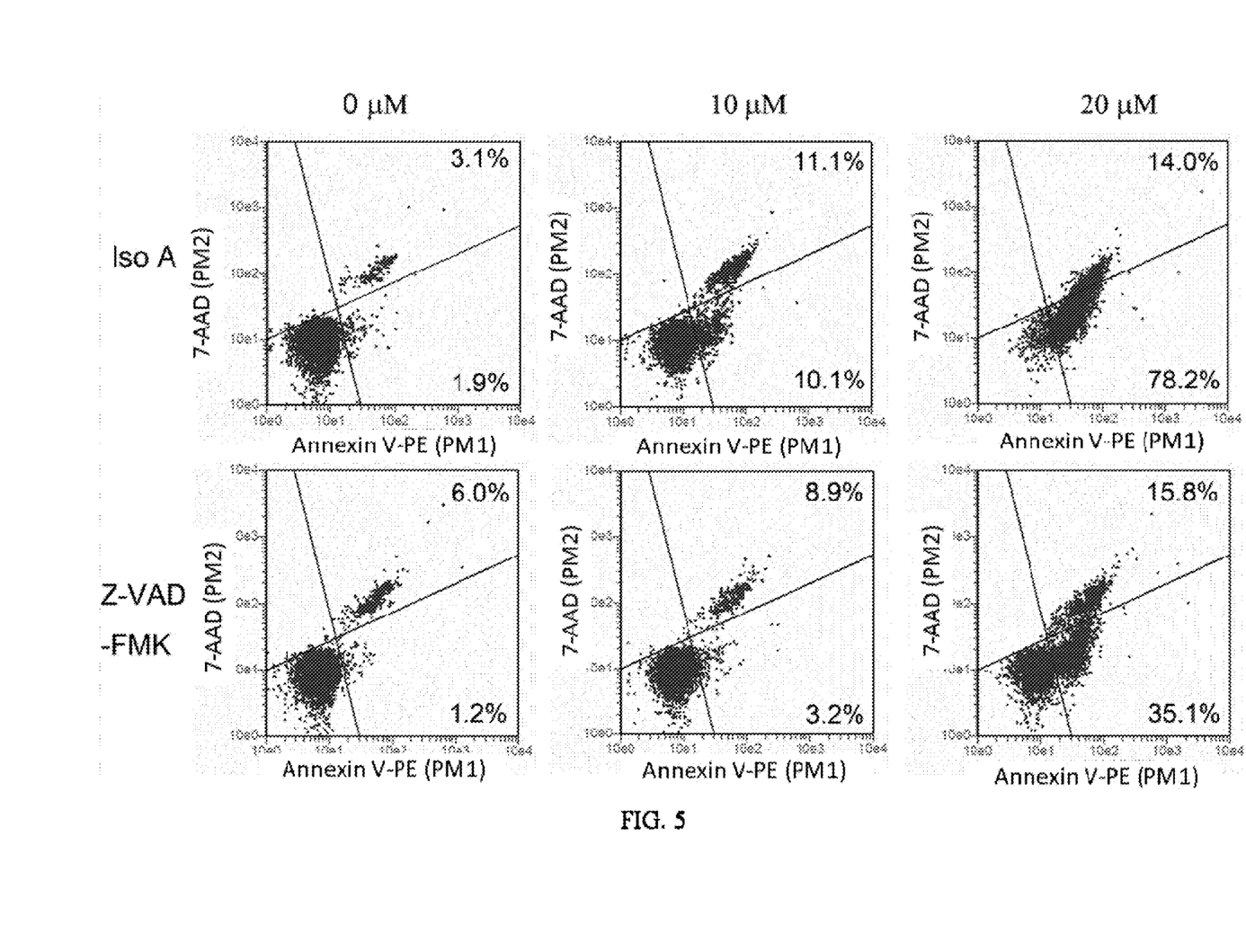
FIG. 5 illustrates the analyzed results of Annexin V after HepG2 cell treated by 10 or 20 μM of Iso A for 24 hours.

Embodiment 3 Iso A can selectively inhibit the growth of human tumor cells and induce apoptosis Dissolving Iso A (purity >99%) in DMSO, and preserving stock solution with concentration of 40 mM in −20° C. Detecting the inhibition effects of Iso A in various cells that includes liver cancer cell, breast cancer cell, lung cancer cell, osteosarcoma cell, melanoma cell, cervical cancer cell etc., and in normal human hepatocyte L02, human embryo lung cell HFL1, human mammary epithelial cell MCF 10A. Compared with normal cells, Iso A shows a stronger inhibition effect on the tumor cells, the IC50 values are all below 30 µM (FIG. 2). Among tested cells, HepG2 cell is the most sensitive to Iso A, thus HepG2 is selected as a model in follow-up experiments. MTT experiment shows that Iso A can inhibit the growth of HepG2 cell in a concentration-dependent manner, but have no obvious inhibitory effects on L02 cell (FIG. 3). Further, trypan blue exclusion assay shows that Iso A can selectively trigger the death of HepG2 cells while being obviously not toxic to normal cells (FIG. 4). Flow cytometry analysis show that the treatment of Iso A leads to increasement of Annexin V positive cells. This result further proves that Iso A induces apoptosis. The pan-caspase inhibitor Z-VAD-FMK partially inhibits the apoptosis induced by Iso A, suggesting that Iso A-induced apoptosis effect is at least partially dependent on the activation of caspase (FIG. 5).

Embodiment 4 Iso A Inhibits Trx1 activity in in vitro reaction

Experiment Material:

Trx1 protein was bought from Sino Biological Inc., Trx1 activity detection kit was bought from American Caymen Chemical cooperation.

Methods for Measuring Trx1 Activity In Vitro:

The in vitro activity of Trx is assayed using the—Thioredoxin Activity Fluorescent Assay Kit (Caymen Chemical). According to the instructions of the kit 2 µl of Iso A with different concentrations (0.195 µM to 100 µM) is added into 0.02 µM Trx mix, following by adding 5 µl of β-NADPH into each sample to incubate in 37° C. for 30 min. Then, a fluorescent substrate is added and Trx1 activity is was recorded as the emission at 518 nm after 488 nm excitation for 30-60 min, with a Thermo Scientific Varioskan Flash fluorescent microplate reader.

Figure 6:
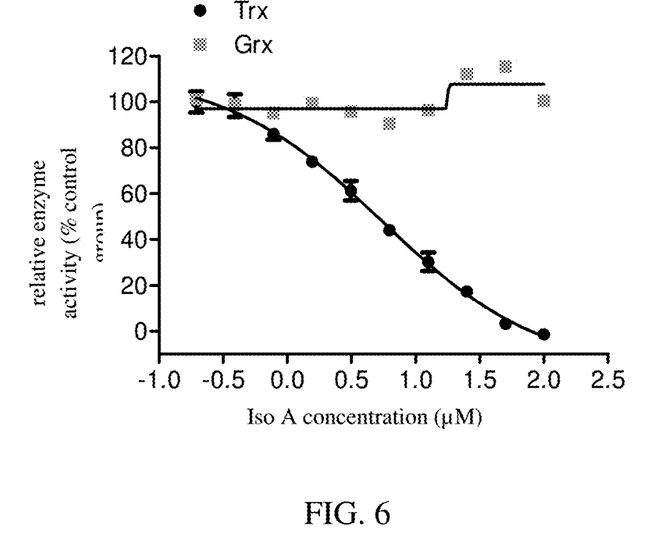
FIG. 6 illustrates the in vitro inhibition of Trx1 activity by Iso A.

Experiment Results:

As shown in FIG. 6, Iso A can inhibit Trx1 activity with respective rate of 20%, 48.6%, 98% in experimental group (2.5, 5, 10 µM), which suggests that the antineoplastic effect of Iso A may be mediated by the inhibition of Trx1 signaling pathway and the regulation of the downstream gene expression.

Embodiment 5 Inhibition on Trx1 by various concentrations of Iso A at cellular level Methods for measuring Trx1 activity in cells or tissue samples: using lysates (20 mM HEPES (pH 7.9), 300 mM NaCl, 100 mM KCl, 10 mM EDTA and 0.1% Nonidet P-40, protease-contained inhibitor) to lyse the cells or tissue samples. Pre-treating 90 µg protein at 37° C. for 15 min by using DTT activation buffer (50 mmol/liter HEPES (pH 7.6), 1 mmol/liter EDTA, 1 mg/ml bovine serum albumin, and 2 mmol/liter dithiothreitol). Then adding 20 µl reaction mixture (200 µl of 1 M HEPES (pH 7.6), 40 µl of 0.2 mol/liter EDTA, 40 µl of NADPH (40 mg/ml)) and 500 µl insulin. Adding 5 µl thioredoxin reductase for initial reaction while adding water of same volume into the control group. Incubate the samples in 37° C. for 20 min, and then add 6 M guanidine hydrochloride of 0.25 ml and 0.4 mg/ml DTNB to terminate reaction. Detecting optical absorption of 412 nm.

Figure 7:
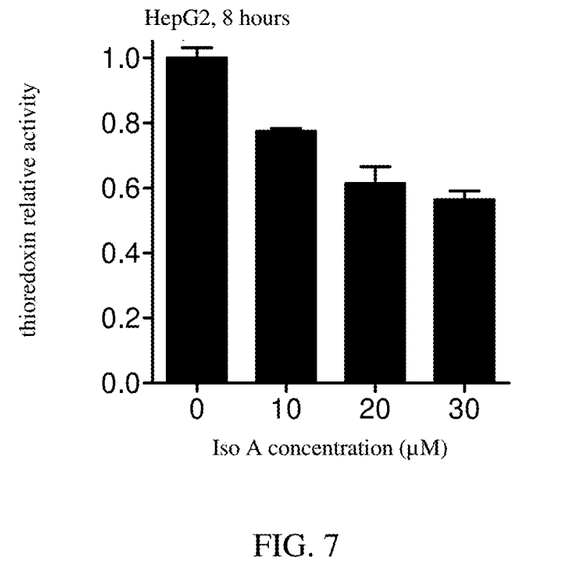
FIG. 7 illustrates activity analysis on Trx1 on HepG2 cell treated by various concentrations of Iso A for 8 hours.

Cultivate human hepatocellular carcinoma cell line HepG2 in vitro culture. When cells have grown into the log phase, the cells are digested by trypin for 5-min-centrifugation (1000 rpm), then discarding the supernatant and diluting the cells as 5×10$^5$ to inoculate on a 6 well culture plate for incubating 24 h, after that, the cells are treated by various concentrations of Iso A (negative control group is 0.5% DMSO) to incubate 16 h in an incubator for recollecting the cells and then detecting Trx1 activity in the cells. Calculate the relative activity of Trx1 in each group under the condition that negative control activity is 1. The results show that Trx1 activity is significantly reduced in HepG2 cells treated with Iso A at 10-30 µM for 8 hours (FIG. 7).

Embodiment 6 Iso A directly conjugates with Trx1 protein at Cys 32/35 residues

Figure 8:
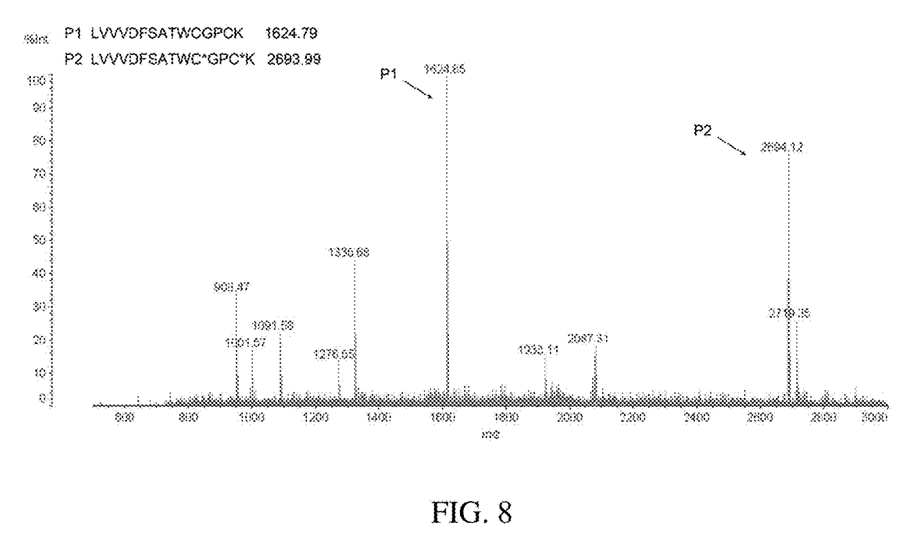
FIG. 8 is a mass spectrum result of the direct conjugation of Iso A with Trx1.

Human-derived Trx1 protein (Sino Biological Inc.) is dissolved in distilled water at a 5 mg/ml and stored. In 25 mM Tris-HCl (pH 7.4) buffer, mixi 4 μl Iso A with 140 μl human Trx1 protein to incubate for 2 h in room temperature. Samples after reaction is treated by Shimadzu Biotech Proteome kit for enzymatic hydrolysis with MonoSpin Trypsin, then desalted by MonoSpin® C18 column for mass spectrometry analysis with MALDI 7090 (SHIMADZU). Results from mass spectrometry analysis show that Iso A can directly bind with Trx1 protein (FIG. 8).

Figure 9:
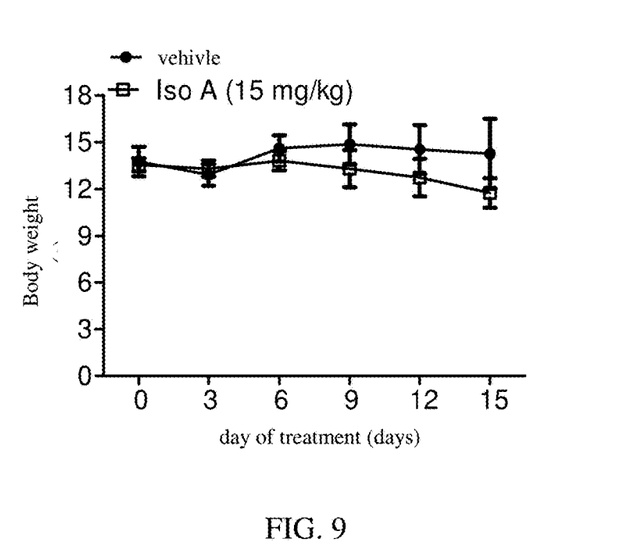
FIG. 9 illustrates weight changes of mice administrated with Iso A or the vehicle control in implanted hepatocellular carcinoma model.

Embodiment 7 Inhibition on the growth of tumor by iso a in a murine xenograft tumor model 1. Material
a) Cell line: Human hepatocellular carcinoma cell line HepG2 is bought from the Cell Bank of Chinese Academy of Sciences for Type Culture Collection
b) Animal: 20 BALB/c male nude mouse with weight of (13±2 g), the BALB/c mice is bought from Model Animal Research Center of Nanjing University, the animal is bred under the environment without a special pathogen in the Animal Center of Jiangsu Traditional Chinese Medicine Research Institution [SCXK(苏) 2002-0001].
c) Pharmaceutical: Iso A 2. Experiment Method:
a) Make of a murine xenograft model ofepatocellular carcinoma: HepG2 cells in log phase are digested with trypin, and suspended with a final density of $2 \times 10^7$ cells/ml. Then, 200 μl (100 μl cells+100 μl matrigel) cell suspension is inoculated into the right subaxillary of nude mice with 1 ml injector.
b) Group and administration of experimental animal: grouping when the tumor becomes 100 mm$^3$ into 10 per group (same average volume per group, too big or small ones are eliminated). Grouping specifically as followings: ① Iso A 15 mg/kg dose group, ② solvent control group (0.5% CMC-Na). Administrate one time every day for total 15 days.
c) Sample selection and index observation:
i. observation for normal state: before drug administration, measure the weight and tumor size (tumor volume V=long diameter×short diameter$^2$/2) one time every day. Observe the locomotor activity, mental state, hair, breath, diet, manure trait and reaction to outside world of the mice. After ending pharmaceutical interference, the mice are anesthetized and the blood is acquired by cardiac puncture. The serum is got by centrifugation and store in −80° C. After the skin of the tumor growing part on the right axilla of the mice is nipped by forceps, use a surgical scissors to cut the skin for exposing the tumor, then use the surgical scissors to dissect the tumor with blunt dissection and use a scale to weigh the tumor, transplanted tumor and calculate the inhibition rate. Antitumor effect is determined by tumor inhibition rate. Tumor inhibition rate (%)=[1−(average weight of tumor in experimental group/average weight of tumor in control group)]×100%
ii. Detecting apoptosis of tumor tissues with TUNEL staining: according to TUNEL apoptosis detection kit specification of Roche Inc. after fixing frozen tissue section in room temperature.
iii. Blood routine examination for assessing the marrow toxicity of Iso A, analyze ALT, AST, ALP level in plasma for assessing hepatotoxicity of Iso A, and measure the creatinine and urea nitrogen for assessing renal damage. Fabricate mice transplanted hepatocellular carcinoma model, and group mice into control group and Iso A (15 mg/kg) administration group at random. Record the weight and tumor size one time every three days and kill the mice after 15-day-administration for detection and analysis of the tumor tissues, blood etc. The results show that during administration, there is no difference in weight between the control group and administration group, which indicates that the toxic and side effects of Iso A are weak (FIG. 9).

Figure 10:
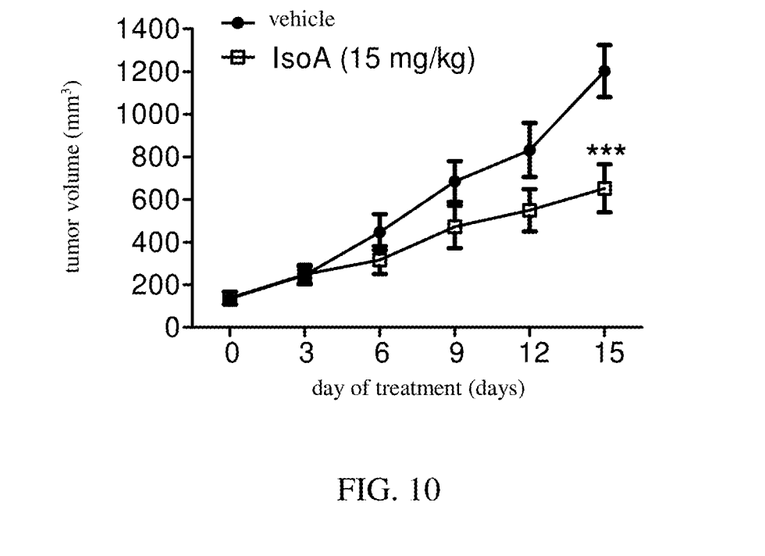
FIG. 10 illustrates tumor volume changes of mice administrated with Iso A or the vehicle control in implanted hepatocellular carcinoma model.
Figure 11:
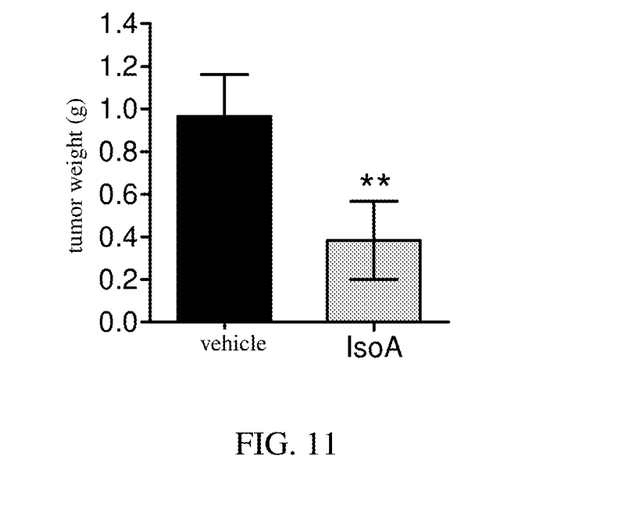
FIG. 11 illustrates tumor weight changes of mice administrated with Iso A or the vehicle control in implanted hepatocellular carcinoma model.
Figure 12:
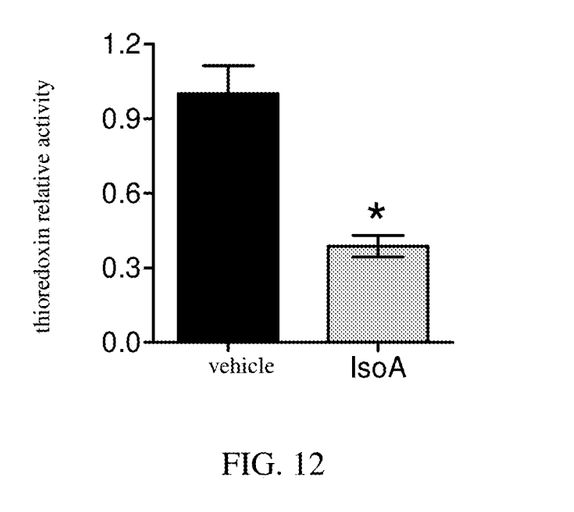
FIG. 12 illustrates Trx1 activity in the xenograft administrated with Iso A or the vehicle control in implanted hepatocellular carcinoma model.

Compared with the control group, the tumor volume and weight have significantly decreased after Iso A administration (FIG. 10, 11). Furthermore, the Trx1 activity in the tumor tissues has significantly decreased through analysis of the Trx1 activity in the tumor tissues (FIG. 12). The above results show that Iso A can take antitumor effect through inhibiting Trx1 activity in the mice model.

Figure 13:
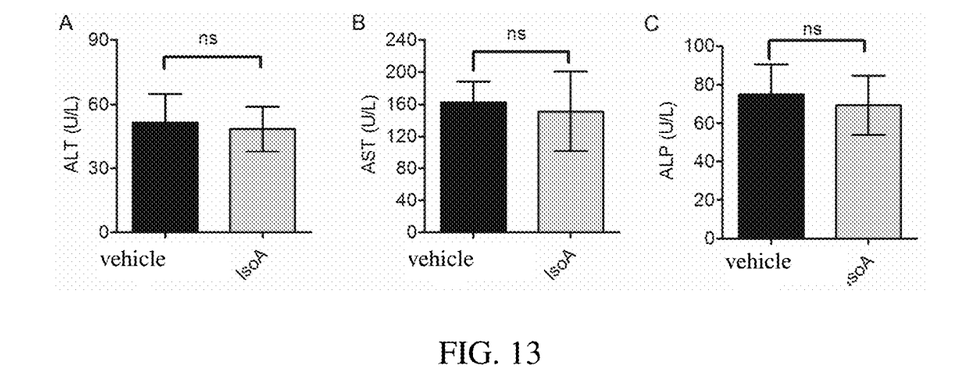
FIG. 13 illustrates index changes of ALT, AST and ALP in serum of mice after drug administration with Iso A.
Figure 14:
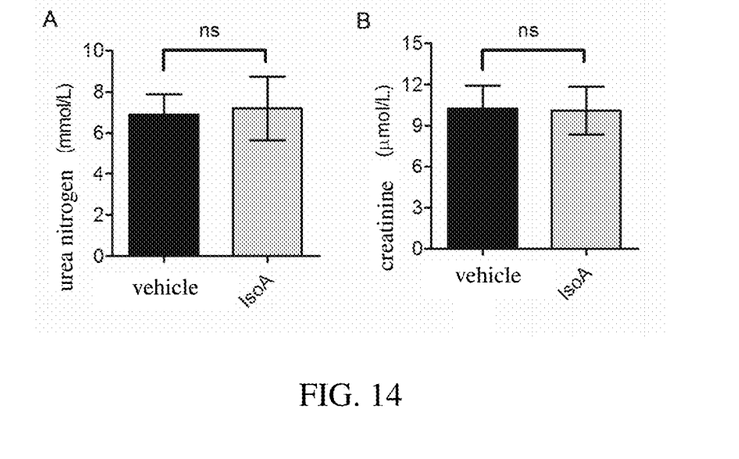
FIG. 14 illustrates index changes of urea nitrogen and creatinine in serum of mice after drug administration with Iso A.
Figure 15:
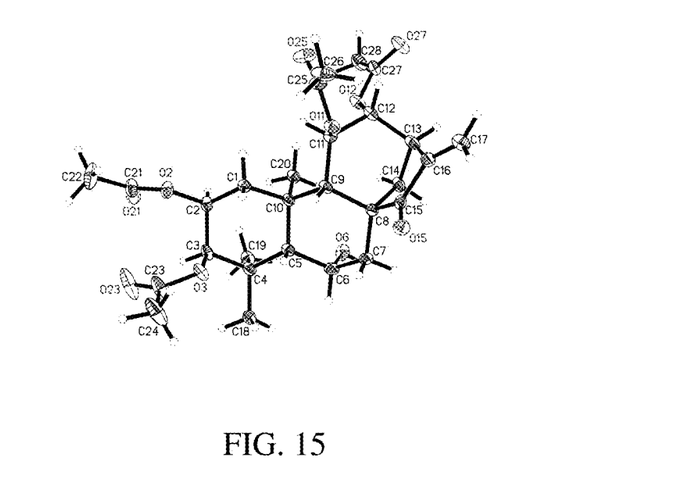
FIG. 15 is an X-ray single crystal diffraction spectrum of Iso A.

There is no obvious difference in ALT, AST and ALP level in serum of the mice in Iso A administration group, which shows that Iso A has no obvious hepatotoxicity (FIG. 13). There is no obvious difference in urea nitrogen and creatinine level in serum of the mice in Iso A administration group, which shows that Iso A has no obvious nephrotoxicity (FIG. 14). The above results show that Iso A has antitumor effects, but no toxic or side effects on several important organs such as marrow, liver and kidney in the xenograft murine models.

Embodiment 8 Preparing Iso A according to embodiment 1, it is added at a ratio of 1:1 by weight to an excipient for granulation and tabletting. The excipient is starch.

Embodiment 9 Preparing Iso A according to embodiment 1, it is added at a ratio of 1:2 by weight to an excipient for granulation and tabletting. The excipient is starch.

Embodiment 10 Preparing Iso A according to embodiment 1, it is made into a capsule by means of the normal capsule preparation method.

Embodiment 11 Preparing Iso A according to embodiment 1, it is made into a tablet by the method as follows:

| Tablet: | Iso A, | 100 mg |
| --- | --- | --- |
| | Starch | Optimum dose |
| | Corn steep liquor | Optimum dose |
| | Magnesium stearate | Optimum dose |

Embodiment 12

| Capsule: | Iso A, | 100 mg |
| --- | --- | --- |
| | Starch | Optimum dose |
| | Magnesium stearate | Optimum dose |

Preparation method: Mixing Iso A with a promoter for sifting to be uniformly mixed in a suitable container, then loading the acquired mixture into a hard gelatin capsule.

Embodiment 13

| Nasal sprays: | Iso A | 80 mg |
| --- | --- | --- |
| | Sodium chloride | 8 mg |
| | EDTA | 1 mg |
| | Sodium phosphate buffer solution (pH 6.5) | 10 mg |
| | Polyethoxy ether | 10 mg |
| | Double distilled water | 2 ml |

Preparation method: Adding one composition into the double distilled water of suitable volume each time while agitating until complete dissolution, then adding another composition. After adding water to 2 ml, this solution is filtered through sterilizing filter for loading into a bottle and being separated due to an appropriate dosage.

Embodiment 14

| Dropping pill: | Iso A, | 100 mg |
| --- | --- | --- |
| | Polyethylene glyco 6000 | 900 mg |

Preparation method: Preparation for the melting liquid of Iso A with polyethylene glyco 6000: after Iso A of above amount being added with appropriate anhydrous ethanol for dissolution in low grade heat, adding it into polyethylene glyco melting liquid (keep warm in 60° C. water bath) of a formulated amount for mixing uniformly by agitation until full volatile of the ethanol, then let it stand for 30 mins in a water bath for removing bubbles, after that loading above uniformly mixed melting liquid without bubbles into a liquid receiver, and dropping the liquid drop by drop into a condensate until completing condensation, then dumping the condensate, collecting the dropping pill and placing it in a silicone dryer for drying or drying naturally after draining and removing the condensate on the dropping pill with a filter paper.

What is claimed is:

1. A compound having Formula I is shown as following:

or the compound having Formula I as pharmaceutically acceptable salt.

2. A preparation method for the compound of Formula I of claim 1, characterized in that, it comprises steps as follows:
   (1) grinding aerial parts of *Isodon forrestii* var. *forrestii* into plant powders;
   (2) soaking the plant powders acquired in step (1) in a mixture of a first organic solvent and water, wherein ratio of the plant powders to the mixture is 1 kilogram to 1-5 liters while the mixture consists of 10-100% the first organic solvent in the water by volume, and a leach solution is obtained by filtering to remove solid parts;
   (3) after the leach solution acquired in step (2) is distilled to remove the first organic solvent, a second organic solvent is added for extraction, wherein the amount of the second organic solvent is 0.2-1 and an extract is obtained after the organic phase is concentrated;
   (4) isolating the compound of Formula I from the extract of step (3) by running a silica gel column chromatography and a reverse phase silica gel column chromatography.

3. The preparation method according to claim 2, wherein the first organic solvent is one or more solvents selected from a group consisting of methanol, ethanol, chloroform, dichloromethane, petroleum ether and acetone.

4. The preparation method according to claim 2, characterized in that, in step (3), the second organic solvent is one or more solvents selected from a group consisting of ethyl acetate, chloroform, ether and petroleum ether.

5. The preparation method according to claim 2, characterized in that, in step (4), the experimental conditions of the silica gel column chromatography are: the pore diameter of filler silica gel is 100-300 mesh, the eluent is a mixture of chloroform and acetone with volume ratio of 1:0-1, the amounts of the eluent is 3-6 times the total amounts of all samples plus silica gel; the experimental conditions of the reverse phase silica gel column chromatography are: the type of the reverse phase silica gel is RP-18, the eluent is a mixture of methanol and water or acetonitrile and water with volume ratio of 10%-100%, the amounts of the eluent is 3-6 times the amounts of used filler RP-18.

6. A method of treating a tumor, comprising administering to a subject in need thereof a therapeutically effective amount of the compound or pharmaceutically acceptable salt thereof of claim 1, wherein the tumor is selected from a group consisting of liver cancer, breast cancer, colorectal cancer, lung cancer, osteosarcoma, melanoma, hepatocellular carcinoma, sarcoma, pancreatic cancer, cervical cancer, prostate cancer and sequamous cell carcinoma.

7. A pharmaceutical composition comprises a therapeutically effective amount of the compound of claim 1 or pharmaceutically acceptable salt thereof, and a pharmaceutically acceptable excipient.

* * * * *